US008232106B2

United States Patent
Choi (10) Patent No.: US 8,232,106 B2
(45) Date of Patent: Jul. 31, 2012

(54) DETECTION METHODS OF PROTEINS ON POLYACRYLAMIDE GELS USING GEL BACKGROUND STAINING AND ORGANIC DYE COMPOSITIONS FOR THE SAME

(75) Inventor: Jung-kap Choi, Gwangju (KR)

(73) Assignee: Industry Foundation of Chonnam National University (KR)

( * ) Notice: Subject to any disclaimer, the term of this patent is extended or adjusted under 35 U.S.C. 154(b) by 275 days.

(21) Appl. No.: 12/863,367

(22) PCT Filed: Oct. 27, 2008

(86) PCT No.: PCT/KR2008/006332
§ 371 (c)(1),
(2), (4) Date: Jul. 16, 2010

(87) PCT Pub. No.: WO2009/091113
PCT Pub. Date: Jul. 23, 2009

(65) Prior Publication Data
US 2011/0053279 A1    Mar. 3, 2011

(30) Foreign Application Priority Data
Jan. 17, 2008  (KR) .................. 10-2008-0005315

(51) Int. Cl.
*G01N 33/68* (2006.01)
*C09B 67/00* (2006.01)
*C07K 1/26* (2006.01)
(52) U.S. Cl. .............. 436/86; 436/164; 436/177; 8/636; 8/657; 8/658; 204/456; 204/463

(58) Field of Classification Search .................. None
See application file for complete search history.

(56) References Cited

U.S. PATENT DOCUMENTS

| | | | | |
|---|---|---|---|---|
| 5,705,649 | A  * | 1/1998 | Shultz et al. | 548/126 |
| 6,277,643 | B1 * | 8/2001 | Choi et al. | 436/86 |
| 6,815,210 | B1 * | 11/2004 | Profitt et al. | 436/86 |
| 6,916,663 | B2 * | 7/2005 | Choi | 436/86 |
| 2006/0057730 | A1 * | 3/2006 | Kosaka | 436/86 |
| 2006/0270051 | A1 * | 11/2006 | Jenkins et al. | 436/86 |

FOREIGN PATENT DOCUMENTS

| KR | 10-2002-0006883 | 1/2002 |
|---|---|---|
| KR | 10-2005-0029544 | 3/2005 |

OTHER PUBLICATIONS

Lin, F. et al. "Detection of Proteins and Sialoglycoproteins in Polyacrylamide Gels Using Eosin Y Stain," The Protein Protocols Handbook, 2nd Ed., Humana Press Inc., Totowa, New Jersey, 2002, pp. 295-297.*
Peter J. Wirth et al., "Staining methods in gel electrophoresis, including the use of multiple detection methods," Journal of Chromatography A, vol. 698, 1995, pp. 123-143.

(Continued)

*Primary Examiner* — Maureen Wallenhorst
*Assistant Examiner* — Michelle Adams
(74) *Attorney, Agent, or Firm* — Cantor Colburn LLP (57) ABSTRACT

Disclosed are a method for detecting proteins on a polyacrylamide gel by background staining method using an organic dye composition containing eosin Y or phloxine B, and the organic dye composition for use in the method, which enables the rapid and simple detection of the protein on the polyacrylamide gel with a high sensitivity.

3 Claims, 5 Drawing Sheets

OTHER PUBLICATIONS

James K. Dzandu et al., "Sodium Dodecyl Sulfate-Gel Electrophoresis: Staining of Polypeptides Using Heavy Metal Salts," Analytical Biochemistry, vol. 174, 1988, pp. 157-167.

SIGMA-Aldrich Safety Data Sheet, according to Regulation (EC) No. 1907/2006, Version 3.0 Revision Date Dec. 29, 2008, Print Date Jul. 15, 2010, "Eosin Y."

Anthony T. Andrews, "Electrophoresis Theory, Techniques and Biochemical and Clinical Applications," Second Edition, Food Research Institute, Reading, Clarendon Press, Oxfod, 1986, pp. 1-59.

International Search Report—PCT/KR2008/006332 dated Apr. 29, 2009.

* cited by examiner

DETECTION METHODS OF PROTEINS ON POLYACRYLAMIDE GELS USING GEL BACKGROUND STAINING AND ORGANIC DYE COMPOSITIONS FOR THE SAME

TECHNICAL FIELD

The present invention relates to the detection of proteins on polyacrylamide gels using gel background staining.

More specifically, it relates to a method for detecting proteins on a polyacrylamide gel through gel background staining using an organic dye composition containing eosin Y or phloxine B, and to the organic dye composition for use in the method.

BACKGROUND ART

Polyacrylamide gel electrophoresis (PAGE) is protein analysis technique useful for separation, identification, and purity and size determination of proteins. Particularly, in sodium dodecyl sulfate-PAGE (SDS-PAGE), proteins are strongly bound to SDS, an anionic surfactant, in a ratio of 1.4:1, so that the protein molecules have negatively charged surfaces and are separated only based on their sizes. The SDS-PAGE is simple and has a high resolution, and thus is widely used as a method for protein analysis (see, A. T. Andrews, Electrophoresis, pp. 1-58).

Most proteins to be analyzed are colorless, and thus require an adequate means for detection. Detection methods that have been reported to date include organic dye staining, silver staining, fluorescence staining and background staining.

Organic dye staining is a detection method of proteins, which includes staining protein bands with an organic dye such as Amido Black 10B, Ponceaus S, Fast Green FCF, or Coomassie Brilliant Blue R (CBBR) [see, *J. of Chromatography A*, 698, 123-143 (1995)]. Particularly, staining with CBBR is relatively simple and cost effective, and thus is commonly used. However, CBBR staining requires a long time (8-12 hours) to perform staining and destaining, and provides a relatively low sensitivity [sensitivity of 50 ng for bovine serum albumin (BSA)]. Silver staining provides the highest sensitivity among non-radiation detection methods, and relies on deposition and reduction of silver [see, *J. of Chromatography A*, 698, 123-143 (1995)]. Although the silver staining method provides such a high sensitivity that the method allows detection of up to 0.1 ng, i.e., femtogram scales, the method requires complicated and multi-step processes. Fluorescence staining is a detection method including labeling proteins to be analyzed with a fluorescence-sensitive dye. Although the fluorescence staining method provides a high sensitivity, the method requires complicated process, ultraviolet (UV) irradiation, and precise instruments for quantification, and thus is not cost effective.

Background staining is limited onto SDS-containing gels, and includes forming precipitates on the surface of gels except protein bands with a metallic salt. Although the background staining method allows detection in a short time and has improved applicability, the method shows a short retention time of staining, and has difficulty in storage [see, *Anal. Biochem.* 174, 157-167 (1988)]. Therefore, there has been a continuous demand for a rapid and simple detection method of proteins on polyacrylamide gels, which provides a higher sensitivity as compared to the prior detection methods.

Eosin Y (Acid Red 87, C. I. 45380) is a water-soluble yellowish red dye emitting green fluorescence ($\lambda_{max}=514$ nm) and is represented by the following Formula 1:

[Formula 1]

Phloxine B (Acid Red 92, C. I. 45410) is a water-soluble orange dye represented by the following Formula 2:

[Formula 2]

Both eosin Y and phloxine B contain a carboxyl group, and thus are classified as acidic dyes like CBBR. In histochemical staining, eosin Y is the most commonly used counter-dye against alum hematoxylin for H&E (heamtoxylin & eosin Y) staining method. It is also used as a counter-dye in Gram-Weigert method for Gram-positive bacteria, and it constitutes Papanicolaou's EA solution for staining exfoliated cytologic specimens. Further, it is used in Romanowsky staining method (see, Lillie, R. D. 1977, H. J. Conn's Biological Stains, 9th edition, p. 335-344, Williams Wilkins, Baltimore, Md.). Eosin Y was used in staining proteins on polyacrylamide gels for the first time (see, Lin, F., W. Fan and G. E. Wise, 1991, Eosin Y staining of proteins in polyacrylamide gels, *Anal. Biochem.* 196: 279-283). Phloxine B is a non-toxic dye used as an additive for foods, pharmaceuticals and cosmetics, and is used as a substitute for Gram staining (see, Rasooly R. 2007, Phloxine B, a versatile bacterial stain. *FEMS Immunol. Med. Microbiol.* 49: 261-265).

The present inventors developed a method for detecting proteins on a polyacrylamide gel, which includes staining the polyacrylamide gel with a composite dye composition containing an acidic organic dye and a basic organic dye, as well as a composite dye composition for use therein, and obtained Korean Patent No. 298,471 and U.S. Pat. No. 6,277,643 therefor.

Further, they developed a method for quantifying a protein, which includes reacting 0.001-0.006% (w/v) of eosin Y with the protein in an acidic solution with a pH of 2.2-3.8 to form a protein-eosin Y complex, and measuring the absorbance of the protein-eosin Y complex at a wavelength of 530-555 nm, and obtained Korean Patent No. 303,102 therefor. However, the aforementioned method employs a composite dye composition containing two or more organic dyes, or relates to the quantification of proteins with eosin Y. Thus, those methods are irrelevant to the detection of a protein disclosed herein, which includes detecting the protein on a polyacrylamide gel by background staining with an organic dye composition containing eosin Y or phloxine B.

DISCLOSURE

Technical Problem

In order to solve the above described problems of the prior arts and to provide a novel staining method with improved sensitivity, the present inventors had performed extensive studies. As a result, they found that the above purpose could be attained by detecting proteins on a polyacrylamide gel by background staining with a given concentration of eosin Y or phloxine B, and thus, completed the present invention.

Accordingly, an object of the present invention provides a method for detecting proteins on a polyacrylamide gel by background staining with an organic dye composition containing eosin Y or phloxine B.

Another object of the present invention provides an organic dye composition for use in the method.

Technical Solution

One aspect of the present invention relates to a method for detecting proteins on a polyacrylamide gel, which comprises:

1) adding an organic dye composition containing 0.1-1.5% (w/v) of eosin Y or phloxine B onto the polyacrylamide gel containing the protein to stain background of the gel; and 2) washing the gel of step 1) to remove the dye remaining or bound to the protein therefrom.

Another aspect of the present invention relates to an organic dye composition for use in the method, which comprises 0.1-1.5% (w/v) of eosin Y or phloxine B.

DESCRIPTION OF DRAWINGS

Description will now be made in detail with reference to certain example embodiments illustrated in the accompanying drawings which are given hereinbelow by way of illustration only, and thus are not limitative of the method and dye composition disclosed herein, and wherein.

BEST MODE

Hereinafter, reference will now be made in detail to various embodiments, examples of which are illustrated in the accompanying drawings and described below. While the invention will be described in conjunction with example embodiments, it will be understood that the present description is not intended to be limitative.

This invention relates to a method for detecting proteins on a polyacrylamide gel by background staining method using a specific composition of organic dyes, in a rapid and simple manner with high sensitivity, and the composition of organic dyes for use in the method.

Hereinafter, "eosin Y background staining method" and "phloxine B background staining method" will be described separately.

(1) Eosin Y Background Staining Method

A polyacrylamide gel containing proteins is fixed in acetic acid-containing aqueous ethanol solution and washed with water and aqueous methanol solution, and then, eosin Y is applied thereto for staining. As a result, in the presence of eosin Y at a concentration less than 0.1% (w/v), the protein is stained and turns into pink, so that the protein can be detected by color but merely with similar sensitivity to that of CBBR staining. In contrast, when the concentration of eosin Y is increased to 0.1% (w/v) or higher, background is stained with a sensitivity of about 60-320 fold higher than that of CBBR staining, and about 10 fold higher than that of the prior background staining, zinc-imidazole staining method.

Additionally, it shows a high reaction rate and enables the detection within 50 minutes with omitting destaining for a long time.

In the background staining method according to the present invention, the concentration of the dye would be critical and the composition of the staining solution would be important as well. Examples of factors that may affect the staining include the concentration of the dye, kind and content of an alcohol used as a solvent, pH, and the like.

Considering all of these factors, eosin Y may be used at a concentration of 0.1-1.5% (w/v), and particularly, 0.3% (w/v). When eosin Y is used at a concentration less than 0.1% (w/v) or greater than 1.5% (w/v), the intensity difference between the protein band and the background may be decreased undesirably. It can be seen from FIG. 1 that shows the intensities of protein bands depending upon the concentration of eosin Y.

In a preferable embodiment, the staining may be performed after removing interfering substances such as buffer or SDS by fixing and washing, following electrophoresis. For fixing, 5-15% (v/v) acetic acid-containing 30-60% (v/v) aqueous ethanol solution, particularly 10% (v/v) acetic acid-containing 50% (v/v) aqueous ethanol solution, may be used, and for washing, water and 30-50% (v/v) aqueous methanol solution, particularly 50% (v/v) aqueous methanol solution, may be used sequentially.

The dye composition for use in the method of the present invention may be obtained by adding eosin Y to an acetic acid-containing aqueous methanol solution as a solvent.

Particularly, in order to improve the staining effect, eosin Y may be added to 0.1-2% (v/v) acetic acid-containing 30-60% (v/v) aqueous methanol solution as a solvent. In order to maximize the staining effect, eosin Y may be added to 1% (v/v) acetic acid-containing 50% (v/v) methanol aqueous solution as a solvent. This is because the above-mentioned dye composition allows effective infiltration of the dye into the background gel. Then, the stained gel is introduced into and treated with water to wash off the dye bound to the protein, and the background staining is completed.

(2) Phloxine B Background Staining

A polyacrylamide gel containing proteins is fixed in acetic acid-containing aqueous ethanol solution and washed with water and aqueous methanol solution, and then, phloxine B is applied thereto for staining. As a result, in the presence of phloxine B at a concentration less than 0.1% (w/v), the protein is stained and turns into pink, so that the protein can be detected by color but merely with similar sensitivity to that of CBBR staining. In contrast, when the concentration of phloxine B is increased to 0.1% (w/v) or higher, background is stained with a sensitivity of about 60-320 fold higher than that of CBBR staining, and about 10 fold higher than that of the prior background staining, zinc-imidazole staining method.

Additionally, it shows a high reaction rate and enables the detection within 50 minutes with omitting destaining for a long time.

In the background staining method according to the present invention, the concentration of the dye would be critical and the composition of the staining solution would be important as well. Examples of factors that may affect the staining include the concentration of the dye, kind and content of an alcohol used as a solvent, pH, and the like.

Considering all of these factors, phloxine B may be used at a concentration of 0.1-1.5% (w/v), and particularly, 0.3% (w/v). When phloxine B is used at a concentration less than 0.1% (w/v) or greater than 1.5% (w/v), the intensity difference between the protein band and the background may be decreased undesirably. It can be seen from FIG. 2 that shows the intensities of protein bands depending upon the concentration of phloxine B.

In a preferable embodiment, the staining may be performed after removing interfering substances such as buffer or SDS by fixing and washing, following electrophoresis. For fixing, 5-15% (v/v) acetic acid-containing 30-60% (v/v) aqueous ethanol solution, particularly 10% (v/v) acetic acid-containing 50% (v/v) aqueous ethanol solution, may be used, and for washing, water and 30-50% (v/v) aqueous methanol solution, particularly 50% (v/v) aqueous methanol solution, may be used sequentially.

The dye composition for use in the method of the present invention may be obtained by adding phloxine B to an aqueous methanol solution as a solvent. Particularly, in order to improve the staining effect, phloxine B may be added to 30-60% (v/v) aqueous methanol solution as a solvent. In order to maximize the staining effect, phloxine B may be added to 50% (v/v) methanol aqueous solution as a solvent. This is because the above-mentioned dye composition allows effective infiltration of the dye into the background gel. Then, the stained gel is introduced into and treated with 0.05% aqueous acetic acid solution to wash off the dye bound to the protein, and the background staining is completed.

The present invention will be specifically explained with reference to the following examples, which are provided for the better understanding of the invention but should not be construed to limit the scope of the invention in any manner.

EXAMPLE 1

Detection of BSA by Eosin Y Background Staining (1) Preparation of Gels and Electrophoresis First, SDS-containing slab gels were prepared according to Laemmli's method. Protein concentrations were measured by Bradford's method using Bio-Rad Standard I for quantification of protein (see, Anal. Biochem. 151, 369-374). Before electrophoresis, protein samples, i.e., 250 ng, 125 ng, 62 ng, 31 ng, 15 ng, 8 ng, 4 ng, 2 ng, 1 ng and 0.5 ng of BSA, were heated in a sample buffer (70 mM Tris-HCl, pH 6.8, 11.4% glycerol, 3% SDS, 0.01% bromophenol blue, and β-mercaptoethanol) to 100° C. for 5 minutes. The developing buffer contained 0.025 M Tris, 0.2 M glycine and 0.1% SDS, and had a pH of 8.3. The gel had a thickness of 1 mm, and stacking gels (4.5%) with a length of 1.5 cm were stacked on separating gels (10%) with the ratio of acrylamide:bisacryamide of 30:0.8.

Then, 250 ng, 125 ng, 62 ng, 31 ng, 15 ng, 8 ng, 4 ng, 2 ng, 1 ng and 0.5 ng of BSA were loaded onto wells in order from the left. Then, electrophoresis was carried out in a Mini Protein II slab gel system at 200 V for 35 minutes.

(2) Staining and Washing

To elevate the staining effect, the gels separated by electrophoresis were fixed with agitation in 10% (v/v) acetic acid-containing 50% (v/v) aqueous ethanol solution for 20 minutes. Then, the gels were washed with water twice, for 2 minutes each time, and then with 50% (v/v) aqueous methanol solution for about 10 minutes.

The time for fixing, washing and staining was adjusted as shown in the following Table 1. The gels were washed with the washing solution having the composition as described in Table 1 to remove interfering substances such as buffer and SDS.

Then, the gels were stained with the dye composition as described in Table 1, with agitation in an agitator for about 10 minutes. The dye composition was prepared just prior to use by dissolving eosin Y into 1% (v/v) acetic acid-containing 50% (v/v) aqueous methanol solution. The stained gels required no destaining, and were treated with water for about 5 minutes to remove the dye remaining or bound to the protein. The stained gels could be observed on the black background, and they could be observed even after several days. In scanning, the gels were scanned on the black background, or by using a negative scanner.

TABLE 1

| Dye | Final Concentration (% w/v) (Optimum Concentration (% w/v)) | Step | Compositions of Solutions for Fixing, Washing and Staining | Time (min) | Sensitivity (ng) |
|---|---|---|---|---|---|
| Eosin Y | 01-15 (0.3) | | Acetic acid/ethanol/water | | 0.1 |

TABLE 1-continued

| Dye | Final Concentration (% w/v) (Optimum Concentration (% w/v)) | Step | Compositions of Solutions for Fixing, Washing and Staining | Time (min) | Sensitivity (ng) |
|---|---|---|---|---|---|
| | | Fixing | 10/50/40 Acetic acid/methanol/water | 20 | |
| | | Washing 1 | 0/0/100 | 2x2 | |
| | | Washing 2 | 0/50/50 | 10 | |
| | | Staining | 1/50/49 | 10 | |
| | | Washing 3 | 0/0/100 | 5 | |

Figure 1:
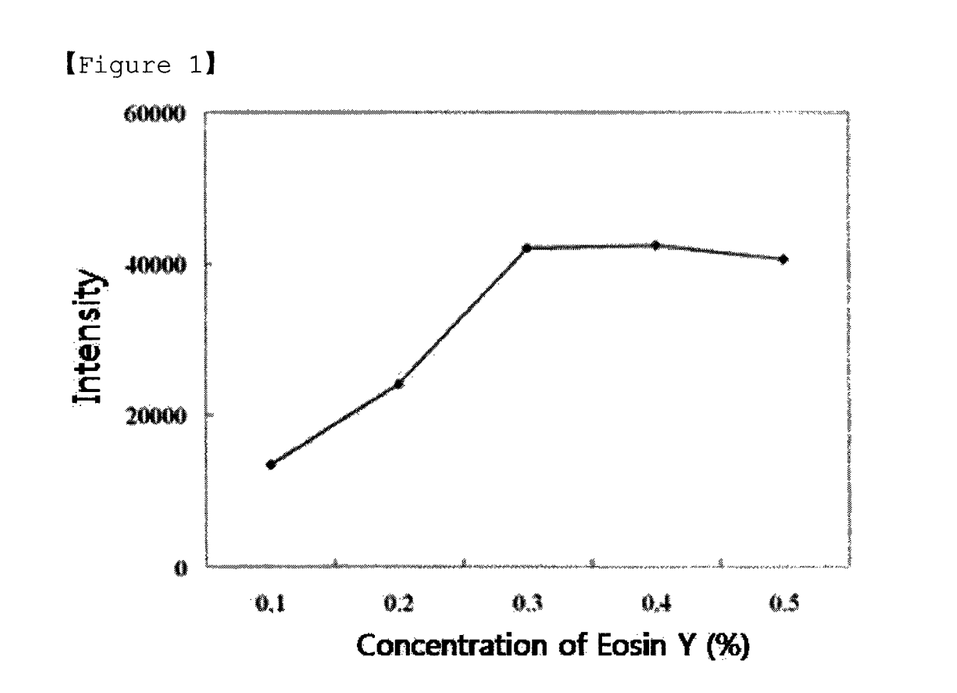
FIG. 1 is a graph showing the intensities of protein bands stained by background staining method using various concentrations of eosin Y, following SDS-polyacrylamide gel electrophoresis.
Figure 3:
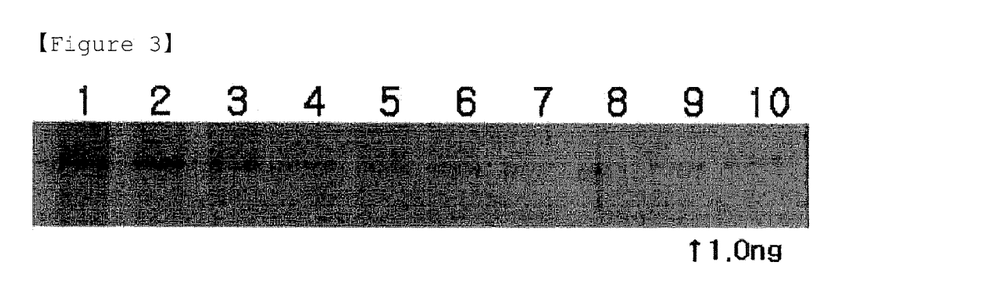
FIG. 3 is a photography showing the detection sensitivity of BSA (bovine serum albumin) protein on SDS-polyacrylamide gels, by background staining method with eosin Y.

The results of staining with various concentrations of eosin Y are shown in FIG. 1. As shown in FIG. 1, the preferable concentration of eosin Y was in the range of 0.1-1.5% (w/v), and the most preferable concentration of eosin Y was 0.3% (w/v). The results of staining with 0.3% (w/v) eosin Y were shown in FIG. 3. As shown in FIG. 3, background staining with eosin Y allowed visualization of up to 1.0 ng of BSA, while CBBR staining allowed visualization of up to 62 ng of BSA (see FIG. 5). It could be seen from the above results that the background staining with eosin Y has the sensitivity of about 60 fold higher than that of CBBR staining.

EXAMPLE 2

Detection of BSA by Phloxine B Background Staining Method (1) Preparation of Gels and Electrophoresis First, SDS-containing slab gels were prepared according to Laemmli's method. Protein concentrations were measured by Bradford's method using Bio-Rad Standard I for quantification of protein (see, *Anal. Biochem.* 151, 369-374). Before electrophoresis, protein samples, i.e., 250 ng, 125 ng, 62 ng, 31 ng, 15 ng, 8 ng, 4 ng, 2 ng, 1 ng and 0.5 ng of BSA, were heated in a sample buffer (70 mM Tris-HCl, pH 6.8, 11.4% glycerol, 3% SDS, 0.01% bromophenol blue, and β-mercaptoethanol) to 100° C. for 5 minutes. The developing buffer contained 0.025 M Tris, 0.2 M glycine and 0.1% SDS, and had a pH of 8.3. The gel had a thickness of 1 mm, and stacking gels (4.5%) with a length of 1.5 cm were stacked on separating gels (10%) with the ratio of acrylamide:bisacryamide of 30:0.8.

Then, 250 ng, 125 ng, 62 ng, 31 ng, 15 ng, 8 ng, 4 ng, 2 ng, 1 ng and 0.5 ng of BSA were loaded onto wells in order from the left. Then, electrophoresis was carried out in a Mini Protein II slab gel system at 200 V for 35 minutes.

(2) Staining and Washing

To elevate the staining effect, the gels separated by electrophoresis were fixed with agitation in 10% (v/v) acetic acid-containing 50% (v/v) aqueous ethanol solution for 20 minutes. Then, the gels were washed with water twice, for 5 minutes each time, and then with 50% (v/v) aqueous methanol solution for about 10 minutes.

The time for fixing, washing and staining procedure was adjusted as shown in the following Table 2. The gels were washed with the washing solution having the composition as described in Table 2 to remove interfering substances such as buffer and SDS. Then, the gels were stained with the dye composition as described in Table 2, with agitation in an agitator for about 10 minutes. The dye composition was prepared just prior to use by dissolving phloxine B into 50% (v/v) aqueous methanol solution. The stained gels required no destaining, and were treated with 0.05% aqueous acetic acid solution for about 0.5 minutes to remove the dye remaining or bound to protein. The stained gels could be observed on the black background, and it could be observed even after several days. In scanning, the gels were scanned on the black background, or by using a negative scanner.

TABLE 2

| Dye | Final Concentration (% w/v) (Optimum Concentration (% w/v)) | Step | Compositions of Solutions for Fixing, Washing and Staining | Time (min) | Sensitivity (ng) |
|---|---|---|---|---|---|
| Phloxine B | 0.1-1.5 (0.3) | | Acetic acid/ethanol/water | | 0.1 |
| | | Fixing | 10/50/40 Acetic acid/methanol/water | 20 | |
| | | Washing 1 | 0/0/100 | 5x2 | |
| | | Washing 2 | 0/50/50 | 10 | |
| | | Staining | 0/50/50 | 10 | |
| | | Washing 3 | 0.05/0/99.95 | 0.5 | |

Figure 2:
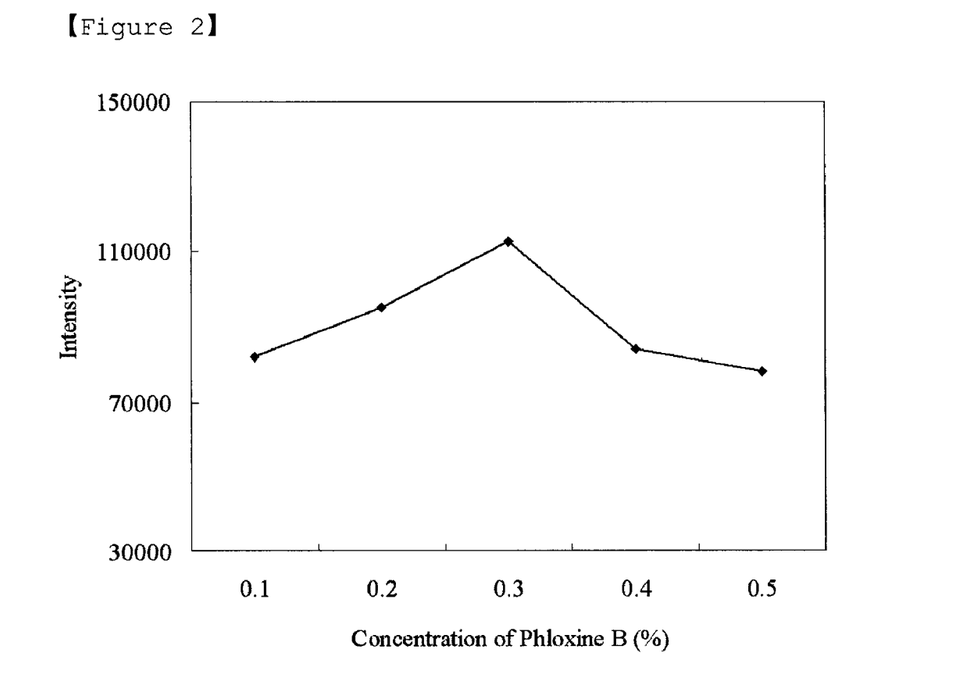
FIG. 2 is a graph showing the intensities of protein bands stained by background staining method using various concentrations of phloxine B, following SDS-polyacrylamide gel electrophoresis.
Figure 4:
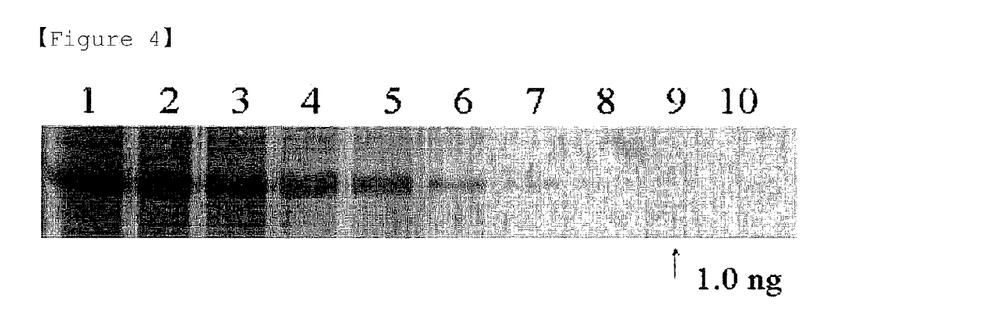
FIG. 4 is a photography showing the detection sensitivity of BSA on SDS-polyacrylamide gels, by background staining method with phloxine B.

The results of staining with various concentrations of phloxine B are shown in FIG. 2. As shown in FIG. 2, the preferable concentration of phloxine B was in the range of 0.1-1.5% (w/v), and the most preferable concentration of phloxine B was 0.3% (w/v). The results of staining with 0.3% (w/v) phloxine B were shown in FIG. 4. As shown in FIG. 4, background staining with phloxine B allowed visualization of up to 1.0 ng of BSA, while CBBR staining allowed visualization of up to 62 ng of BSA (see FIG. 5). It could be seen from the above results that the background staining with phloxine B has the sensitivity of about 60 fold higher than that of CBBR staining.

EXAMPLES 3 AND 4

Detection of Protein Standards by Eosin Y and Phloxine B Background Staining Methods The substantially same procedures as described in Examples 1 and 2 were performed, except that protein standards containing equal amounts of myosin (205 kDa), β-galactosidase (116 kDa), phosphorylase b (97.4 kDa), BSA (66 kDa), ovalbumin (45 kDa) and carbonic anhydrase (29 kDa) were loaded onto wells, at amounts of 200 ng, 80 ng, 32 ng, 12 ng, 5 ng, 2 ng, 0.8 ng, 0.3 ng, 0.1 ng and 0.04 ng, in order from the left.

Figure 6:
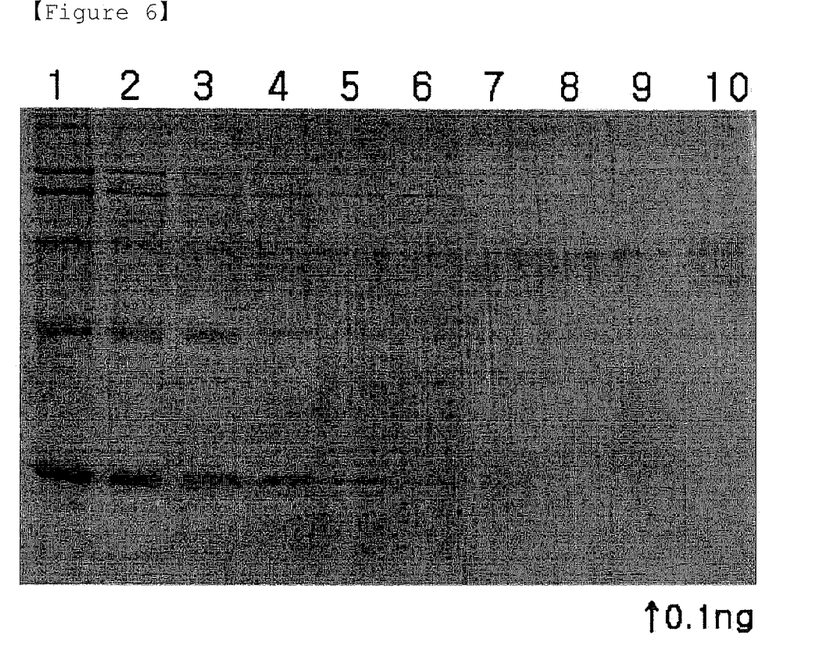
FIG. 6 is a photography showing the detection sensitivity and staining pattern of protein standards on SDS-polyacrylamide gels, by background staining method with eosin Y.
Figure 7:
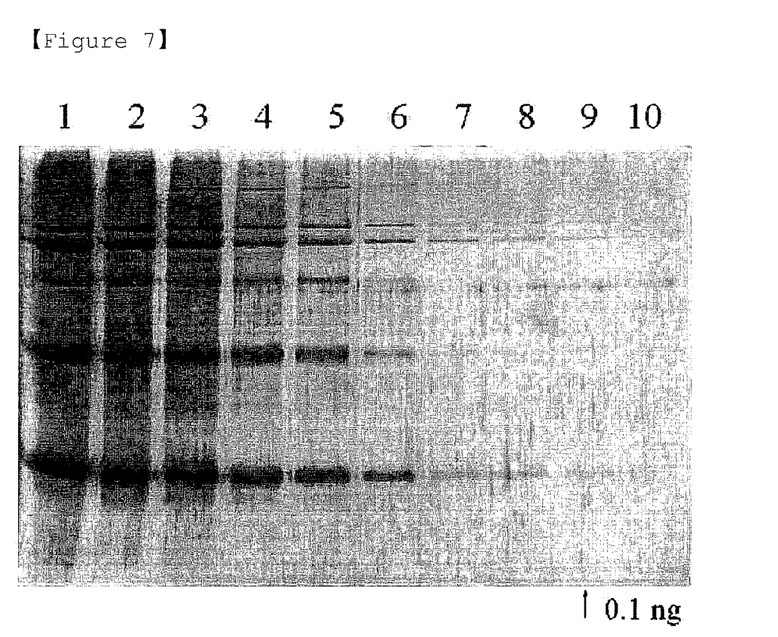
FIG. 7 is a photography showing the detection sensitivity and staining pattern of protein standards on SDS-polyacrylamide gels, by background staining method with phloxine B.

The results are shown in FIGS. 6 and 7. As shown in FIGS. 6 and 7, background staining methods with eosin Y and phloxine B showed similar staining patterns to those of CBBR, zinc-imidazole and Sypro® Ruby staining methods (see, FIGS. 8-10).

However, the background staining methods with eosin Y and phloxine B allowed detection of the protein standards up to 0.1 ng. Therefore, it can be seen from the above results that the background staining methods using eosin Y and phloxine B has the sensitivity of about 320 fold higher than that of CBBR staining method (up to 32 ng), about 10 fold higher than that of zinc-imidazole background staining method (up to 1.0 ng), and about 10 fold higher than that of Sypro® Ruby fluorescent staining method (up to 1.0 ng).

COMPARATIVE EXAMPLE 1

Detection of BSA by CBBR Staining Method

Figure 5:
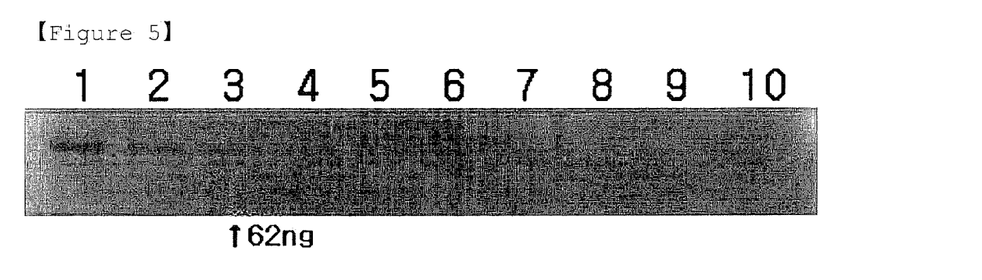
FIG. 5 is a photography showing the detection sensitivity of BSA on SDS-polyacrylamide gels, by CBBR staining method.

The substantially same procedures as described in Example 1 were performed, except that 0.2% (w/v) CBBR-250 solution was used as the dye, and the gels were fixed for 1 hour in 7% (v/v) acetic acid-containing 40% (v/v) aqueous methanol solution as the solvent, stained for 1 hour, and destained for at least 2 hours. The results are shown in FIG. 5. As shown in FIG. 5, CBBR staining method allowed detection of BSA up to 62 ng.

COMPARATIVE EXAMPLE 2

Detection of Protein Standards by CBBR Staining Method

Figure 8:
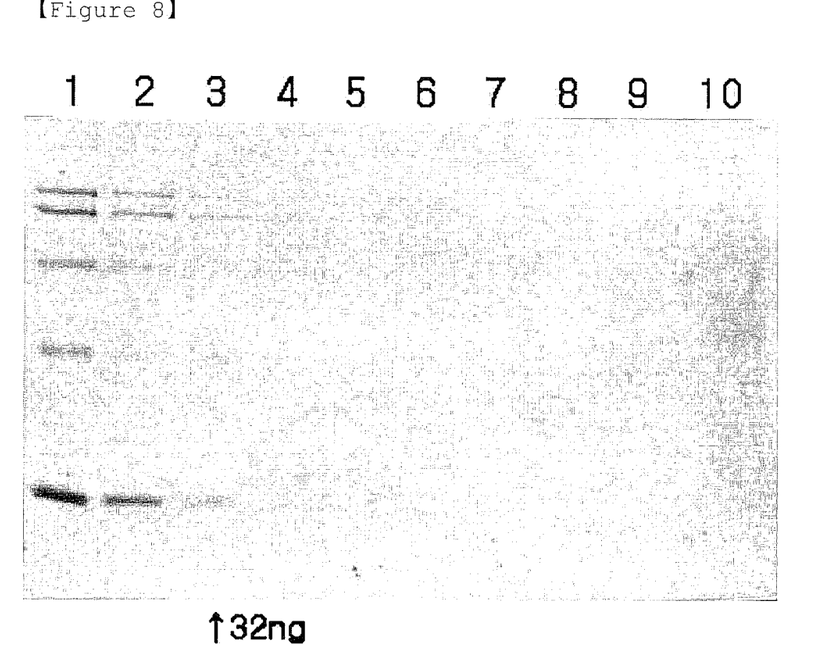
FIG. 8 is a photography showing the detection sensitivity and staining pattern of protein standards on SDS-polyacrylamide gels, by CBBR staining method.

The substantially same procedures as described in Example 3 were performed, except that 0.2% (w/v) CBBR-250 solution was used as the dye, and the gels were fixed for 1 hour in 7% (v/v) acetic acid-containing 40% (v/v) aqueous methanol solution as the solvent, stained for 1 hour, and destained for at least 2 hours. The results are shown in FIG. 8. As shown in FIG. 8, CBBR staining allowed detection of the protein standards up to 32 ng.

COMPARATIVE EXAMPLE 3

Detection of Protein Standards by Zinc-Imidazole Background Staining Method

Figure 9:
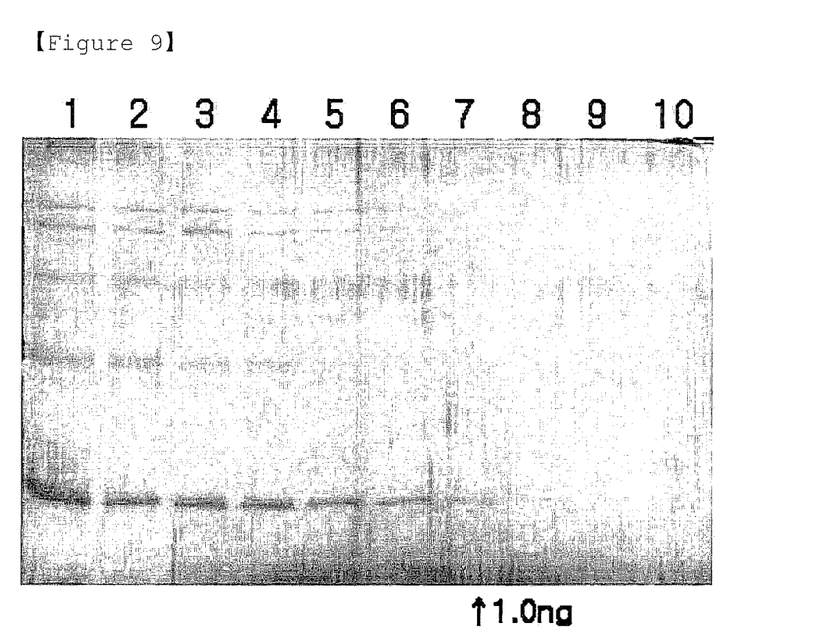
FIG. 9 is a photography showing the detection sensitivity and staining pattern of protein standards on SDS-polyacrylamide gels, by zinc-imidazole staining method.

The substantially same procedures as described in Example 3 were performed, except that the gels were washed with distilled water for 30 seconds following electrophoresis, and the gels were reacted in a solution of 0.2 M imidazole and 0.1% (w/v) SDS for about 15 minutes, and then in 0.2 M zinc sulfate solution until the background of the gels turned into white, followed by washing in distilled water. The results are shown in FIG. 9. As shown in FIG. 9, zinc-imidazole background staining allowed detection of the protein standards up to 1.0 ng.

COMPARATIVE EXAMPLE 4

Detection of Protein Standards by Sypro® Ruby Fluorescence Staining Method

Figure 10:
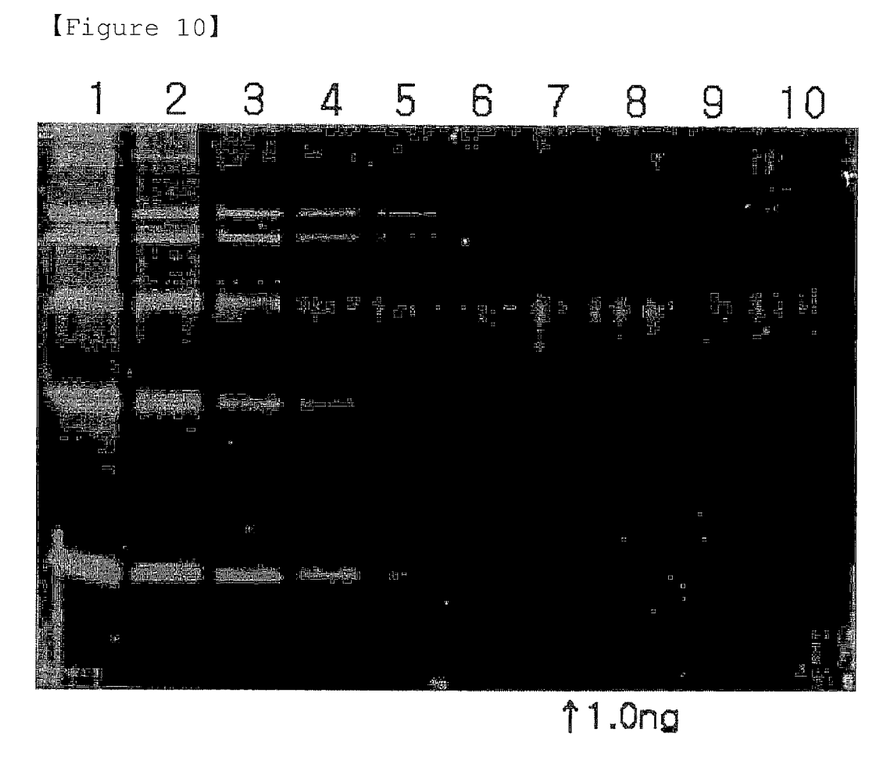
FIG. 10 is a photography showing the detection sensitivity and staining pattern of protein standards on SDS-polyacrylamide gels, by fluorescent staining method with Sypro® Ruby.

The substantially same procedures as described in Example 3 were performed, except that the gels were stained with a commercially available Sypro® Ruby staining solution for at least three hours, and then, washed in 7% (v/v) acetic acid-containing 10% (v/v) aqueous methanol solution for about 30 minutes. The results are shown in FIG. 10. As shown in FIG. 10, Sypro® Ruby fluorescence staining allowed detection of the protein standards up to 1.0 ng.

INDUSTRIAL APPLICABILITY

The present invention enables the simple and rapid (i.e. within 50 minutes) detection of proteins, and shows the detection sensitivity of about 60-320 fold higher than that of CBBR staining method, and about 10 fold higher than those of zinc-imidazole background and Sypro® Ruby fluorescent staining methods, by detecting proteins on polyacrylamide gels with background staining method using a given concentration of eosin Y or phloxine B.

Description was made in detail with reference to example embodiments. However, it will be appreciated by those skilled in the art that changes may be made in these embodiments without departing from the principles and spirit of the method and dye composition disclosed herein, the scope of which is defined in the accompanying claims and their equivalents.

The invention claimed is:
1. A method for detecting proteins in a polyacrylamide gel containing protein bands and a gel background, the method comprising
  1) adding an organic dye composition containing 0.1-1.5% (w/v) of phloxine B onto the polyacrylamide gel to stain the gel background; and
  2) washing the polyacrylamide gel after adding the organic dye composition to remove organic dye composition from the protein bands.
2. The method of claim 1, wherein the organic dye composition containing 0.1-1.5% (w/v) of phloxine B further comprises aqueous methanol solution, the aqueous methanol solution being 30-60% (v/v) methanol.
3. The method of claim 1, wherein the polyacrylamide gel is fixed and washed following an electrophoresis step.

* * * * *